United States Patent [19]

Singh et al.

[11] Patent Number: 4,502,331

[45] Date of Patent: Mar. 5, 1985

[54] METHOD FOR ULTRASONIC INSPECTION OF TURBINE DISC RIMS

[75] Inventors: Gurvinder P. Singh; Richard A. Cervantes, both of San Antonio, Tex.

[73] Assignee: Southwest Research Institute, San Antonio, Tex.

[21] Appl. No.: 532,159

[22] Filed: Sep. 14, 1983

[51] Int. Cl.³ .............................................. G01N 29/04
[52] U.S. Cl. ........................................ 73/627; 73/633
[58] Field of Search ................... 73/627, 629, 633, 640

[56] References Cited

U.S. PATENT DOCUMENTS

| | | |
|---|---|---|
| 2,984,098 | 5/1961 | Loos . |
| 3,756,071 | 9/1973 | Dory . |
| 3,924,456 | 12/1975 | Vahaviolos . |
| 3,995,968 | 12/1976 | Campbell et al. ............... 73/629 |
| 4,052,889 | 10/1977 | Mucciardi et al. . |
| 4,098,129 | 7/1978 | Deblaere et al. . |
| 4,099,416 | 7/1978 | Niklas . |
| 4,106,327 | 8/1978 | Adler et al. . |
| 4,274,288 | 6/1981 | Tittman et al. . |
| 4,292,848 | 10/1981 | Rainey et al. . |

Primary Examiner—Anthony V. Ciarlante
Attorney, Agent, or Firm—Arnold, White & Durkee

[57] ABSTRACT

Low pressure turbine disc rims are inspected by a method in which an ultrasonic beam is directed into a disc rim steeple from a location on the disc rim web. Reflected waves are received and signals indicative thereof are produced for display. A predetermined time window is established on the display, based on the time-of-flight difference between the top of the steeple and the disc rim. The presence of signals within the time window on the display is determined to indicate the presence of a crack. Cracks located along the steeple serrations and oriented in a generally tangential direction to the steeple cross section are detected by producing an ultrasonic beam directed along a line normal to the bottom of a steeple. Cracks located at the bottom of a blade groove at the steeple root and oriented in a generally radially direction can be detected by producing an ultrasonic beam skewed at an acute angle relative to the line normal to the bottom of a steeple.

6 Claims, 13 Drawing Figures

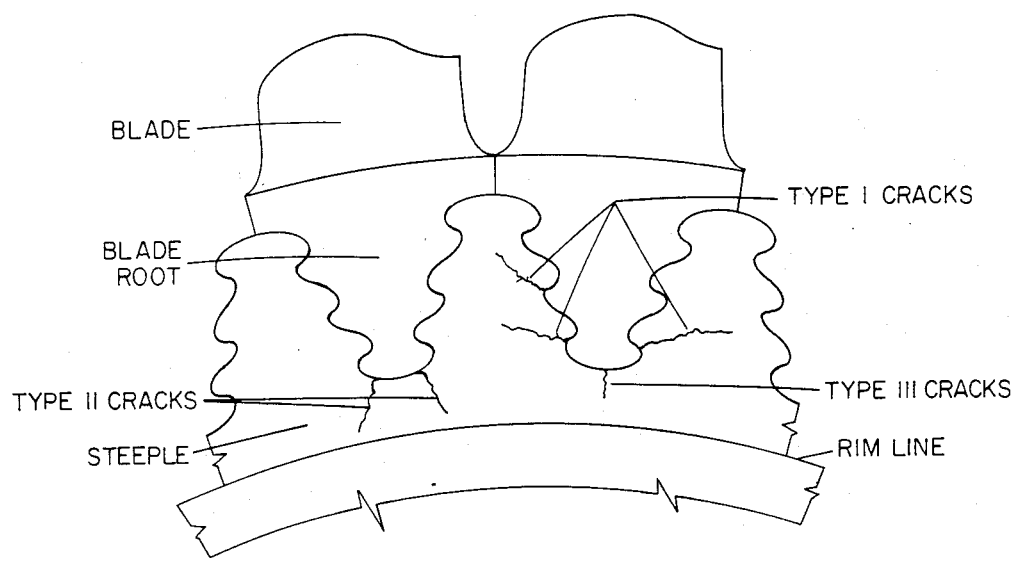
FIG. 1
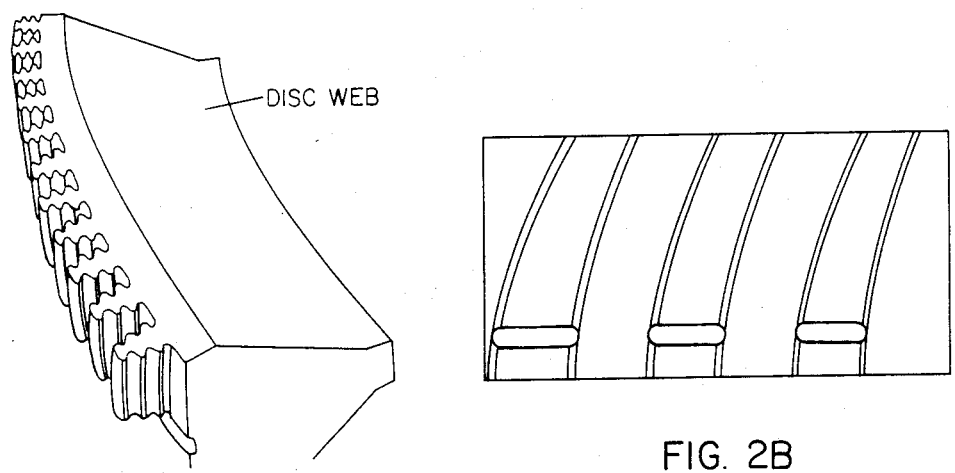
FIG. 2A
FIG. 2B

METHOD FOR ULTRASONIC INSPECTION OF TURBINE DISC RIMS

BACKGROUND OF THE INVENTION

The present invention relates to a method of inspecting turbine disc rims; and more particularly, it relates to an ultrasonic, non-destructive method of inspecting turbine disc rims.

Heretofore, inspection of turbine disc rims for cracks has been by magnetic particle inspection methods. Because the majority of cracks are in an area of the disc rim obscured by attached blades, the magnetic particle inspection method requires the destructive removal of the blades prior to inspection. The requirement for removal of the blades makes the magnetic particle inspection method expensive and time consuming.

BRIEF DESCRIPTION OF THE DRAWINGS

A written description setting forth the best mode presently known for carrying out the present invention, and of the manner of implementing and using it, is provided by the following detailed description which references the attached drawings wherein:

FIG. 1 is a diagram showing the various types of cracks found in turbine disc rim steeples;

FIG. 2(A) is a perspective view of a turbine disc rim segment showing its overall geometry;

FIG. 2(B) is a plan view showing the curvature of the steeples;

DETAILED DESCRIPTION OF THE INVENTION

A. Cracking in Low-Pressure Steam Turbine Rotor Disc

In low-pressure steam turbine rotor discs, cracking in the disc rim area is typically observed in the steeples. Moreover, cracking appears to be of three types according to location and orientation. In FIG. 1, the three types of cracks are illustrated and designated as Type I, Type II, Type III. A definition of each type of crack is as follows:

Type I—Cracks located along steeple serrations and oriented in a generally tangential direction through the steeple cross section.

Type II—Cracks located at the bottom of the blade groove at the steeple root and oriented in a generally radial direction.

Type III—Independent, face-initiated cracks oriented in a generally radial plane and located below the bottom of the blade grooves.

It has been found that 95% of turbine disc rim cracks are of the Type I and II categories, and are some form of stress corrosion cracks.

B. Detection of Type I Cracks

Figure 3:
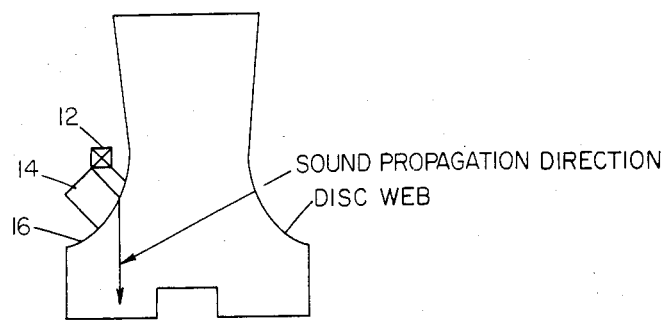
FIG. 3 is a cross section view of the turbine disc rim segment of FIG. 2 illustrating placement of an ultrasonic transducer and shoe thereon for detecting both Type I and Type II cracks.

In FIG. 2(A), a disc rim segment is shown in perspective. This view shows the overall geometry of the disc rim segment. In FIG. 2(B) the disc rim segment is shown in a plan view to illustrate the curvature of the steeples. Referring next to FIG. 3, a cross section view of the disc rim segment further illustrates its geometry and in particular shows the sloping surface that extends below the disc rim steeples (called the disc web). This surface slopes at a 30° angle.

With continuing reference to FIG. 3, in the ultrasonic inspection method of the present invention, the detection of Type I cracks involves ultrasonic scanning of the disc rim on the sloping surface thereof below the disc rim steeples. As indicated, the transducer arrangement produces shear waves traveling in the radial direction. By moving the transducer up and down the sloping surface, the entire length of the steeples can be inspected.

In order to conduct the ultrasonic inspection method, a transducer 12 is mounted on a shoe 14 having a surface so as to produce shear ultrasonic waves at an angle of 60° off vertical. The entire transducer-shoe structure is placed on the web area 16 of the disc. As the transducer-shoe arrangement is moved up and down the sloping surface of the disc web area, ultrasonic reflection signals will be received back at the transducer. These reflected ultrasonic signals will indicate the top and the bottom of the steeple and any cracks existing in between. The reflected signal received by the transducer is processed and applied to a display, such as an oscilloscope, to provide means for visually identifying disc rim cracks.

Figure 4:
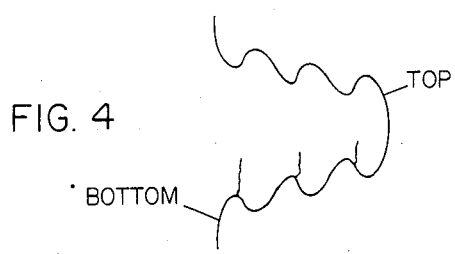
FIG. 4 is a drawing of an illustrative steeple structure having three Type I cracks therein.
Figure 5:
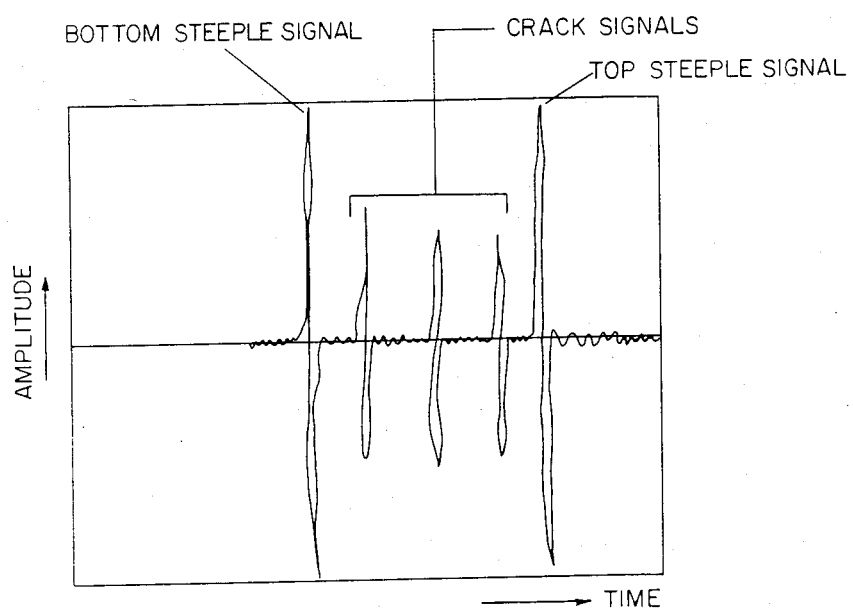
FIG. 5 is an illustration of a oscilloscope display of reflected ultrasonic signals received by a transducer inspecting the steeple shown in FIG. 4 for Type I cracks.

By way of illustration, there is shown in FIG. 4 a steeple having three cracks between the steeple top and bottom. In FIG. 5 there is a drawing of an oscilloscope screen display of reflected ultrasonic signals received by a transducer inspecting the steeple configuration shown in FIG. 4. The oscilloscope display shows the bottom steeple signal and the top steeple signal. The time-of-flight difference between the reflected signals from the steeple top and bottom establishes a time window. Any signals due to cracks will appear within this time window. Because the dimensions of the steeple are known, the time-of-flight difference between the bottom and top steeple signals can be approximated. The time window is typically about 20 microseconds. If reflected ultrasonic signals of any amplitude are detected in the 3.0-4.5 microseconds, 8-11 microseconds, and 14-17 microseconds time ranges relative to the top of steeple signal within the overall time window, the presence of a Type I crack is confirmed. Reflected signals indicated at time periods outside the time ranges are spurious reflections within the steeple structure. For the example as shown in FIG. 4, Type I cracks at locations at the top, middle and bottom serrations will appear on the oscilloscope display at approximately 3.22, 9.77 and 16 microseconds, respectively, with respect to the ultrasonic signal indicating the top of the steeple.

In summary, the ultrasonic method for the detection of Type I cracks involves scanning of a turbine disc rim on the sloping surface below the disc rim steeples using an ultrasonic transducer producing shear waves traveling in a radial direction, and observing a display of reflected signals for the presence of signals within specific time intervals within an overall time window on the display.

C. Detection of Type II Cracks

Figure 6:
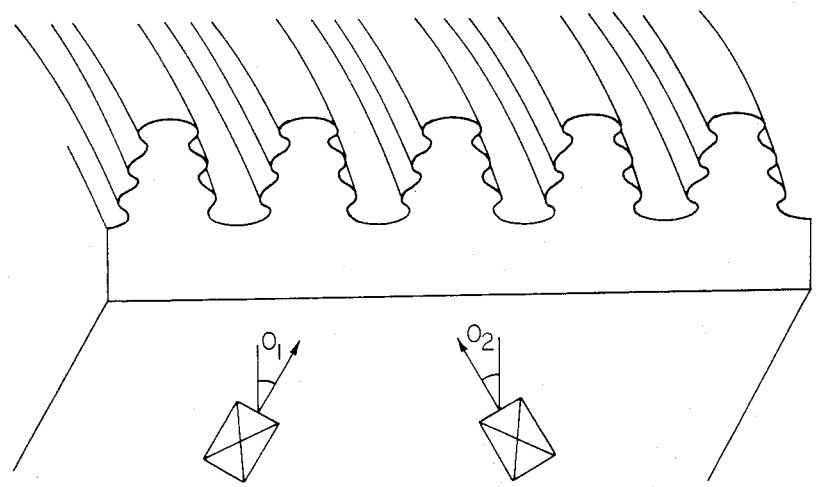
FIG. 6 is a diagram illustrating the orientation of transducers for the detection of Type II cracks on both the concave and convex sides of the steeple.
Figure 7:
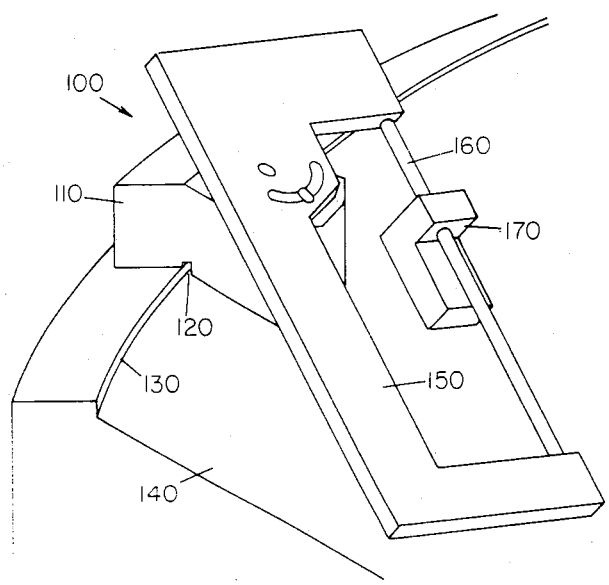
FIG. 7 is a diagram of a fixture for use in maintaining proper transducer orientation while inspecting for Type II cracks.

The detection of Type II cracks using the ultrasonic inspection technique of the present invention also involves scanning of a disc rim on the sloping surface below the disc rim steeples. Similarly, the ultrasonic transducer is mounted on a shoe for disposition at an angle of 60° so as to project waves radially into the disc rim. In conducting the detection method for Type II cracks, the transducer/shoe arrangement is also oriented at a predetermined skewed angle to the disc rim surface as shown in FIG. 6. In order to maintain the desired angle of the transducer/shoe arrangement, a fixture is preferably used. The fixture provides for tracking of the circumferential contour of the disc rim while maintaining the transducer/shoe arrangement at the predetermined skew angle on the sloping rim surface. A suitable fixture structure is shown in FIG. 7. The fixture 100 includes a guide track 110 having a guide surface 120 defined thereon for engaging an edge 130 of the disc rim adjacent sloping surface 140. An angularly adjustable plate 150 is pivotally attached to guide member 110. Plate 150 carries slide bar 160 on which the transducer-mounting shoe 170 is bi-directionally movable. It will be appreciated that the entire fixture 100 can be scanned along the disc circumference with the ultrasonic transducer beam being maintained at a constant angle and depth.

In conducting an inspection for Type II cracks the examination is preferably conducted at various depths in the steeples. Accordingly, the ultrasonic beam of the transducer must be scanned at different spot depths, for example, at 0.5 inch increments on the sloping surface. Also, because Type II cracks may occur on either the concave or the convex side of the steeple, the inspection must be conducted from both sides. That is, the transducer must be scanned at the $\theta_1$ angle shown in FIG. 6 for inspection of the concave side of each steeple, and also it must be scanned at the $\theta_2$ angle for inspection of the convex side of each steeple.

Skewing of the transducer at the angles $\theta_1$ and $\theta_2$ as shown in FIG. 6 optimizes the crack signal while reducing or eliminating the reflections due to steeple and rim surface geometry. Because of the curvature of the steeples, it is necessary to have different examination angles for detection of cracks on either side of a steeple. Preferably, to detect cracks in the concave side of the steeples, the transducer is oriented at a 45° skew angle in the clockwise direction from vertical. That is, the angle $\theta_1$ in FIG. 6 is preferably 45°. When inspecting for cracks on the convex side of the steeple, the transducer is preferably skewed at an angle of 60° in the counter clockwise direction from vertical. That is, the angle $\theta_2$ in FIG. 6 is preferably 60°.

Figure 9:
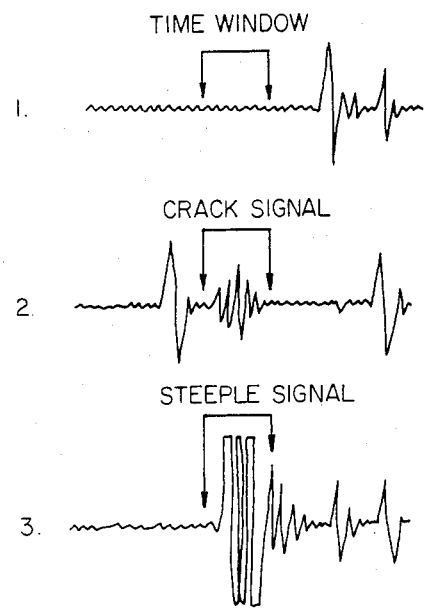
FIG. 9 is a diagram of received reflection signals produced during the scanning operation illustrated in FIG. 8.
Figure 8:
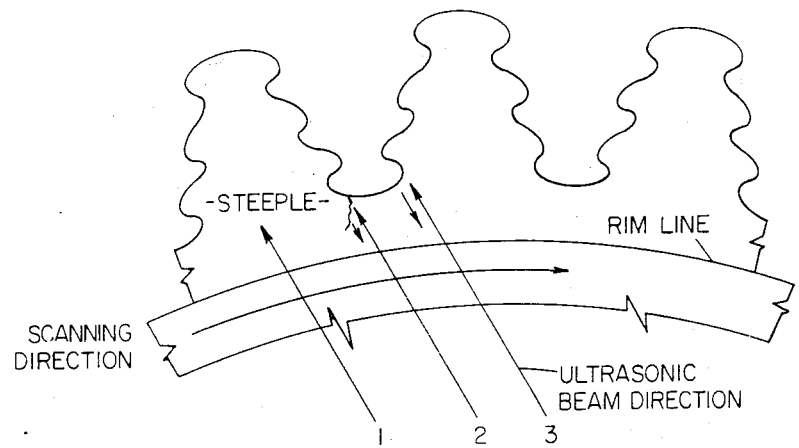
FIG. 8 is a diagram illustrating ultrasonic beam direction through a disc rim during a Type II inspection scanning operation.

The display presentation of received ultrasonic signals during an inspection for Type II cracks depends on whether the examination is being conducted from the concave or the convex side of the steeples. Illustrated in FIGS. 8 and 9 is an inspection conducted from the convex side of the disc rim steeples. FIG. 8 shows a series of displays of received reflected signals corresponding to positions of the ultrasonic beam as it is scanned as shown in FIG. 9. Since the inspection is being conducted from the convex side of the steeples, the crack signal is accompanied by several other signals from geometrical reflectors. The most prominent signal is that received from the concave side of the steeple root. However, this strong geometric reflector produces a regular and predictable pattern when the ultrasonic beam is scanned across several steeples. Thus, a crack present on the convex side of the steeple can be predicted to appear between successive steeple root reflections. Further, an estimate of the time-of-flight to a suspected crack location can be used to determine the cracked signal location on the display. The presence of any signal within a narrow time window centered on the time-of-flight estimate will indicate the presence of a crack. The diagrams of FIG. 8 illustrate these principles of the inspection process.

For cracks detected from the concave side of the steeples, reflected signals will appear singly without interfering steeple root or serration reflections. An estimate of the time-of-flight to a suspected crack location is used to determine the crack signal location on the display. The presence of any signal within a narrow time window centered on the time-of-flight estimate indicates the presence of a crack.

Figure 10A:
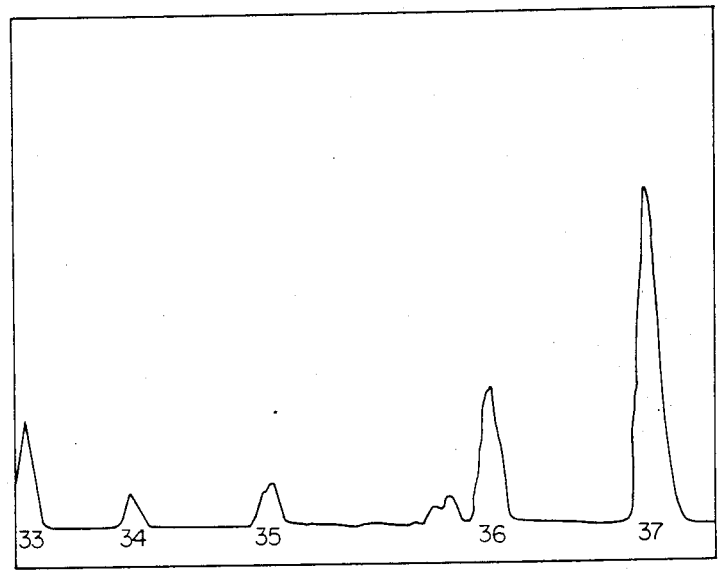
FIGS. 10A and 10B are illustrations of typical Type II inspection scan records obtained from the concave and convex sides, respectively, of the disc rim steeples.
Figure 10B:
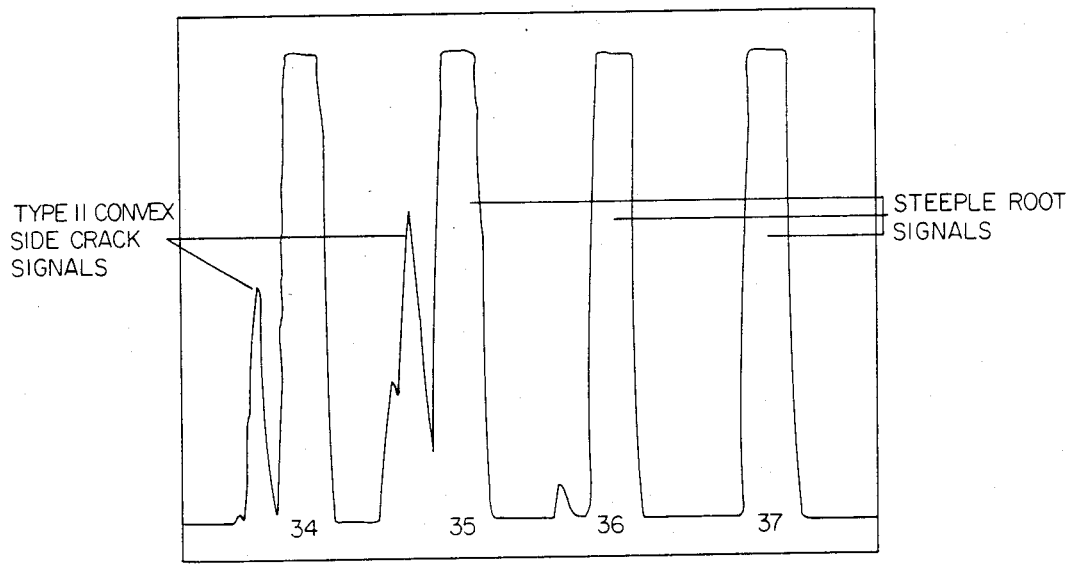

Referring to FIGS. 10A and 10B, there is shown typical Type II crack inspection scan records for the concave and convex sides, respectively.

Figure 11:
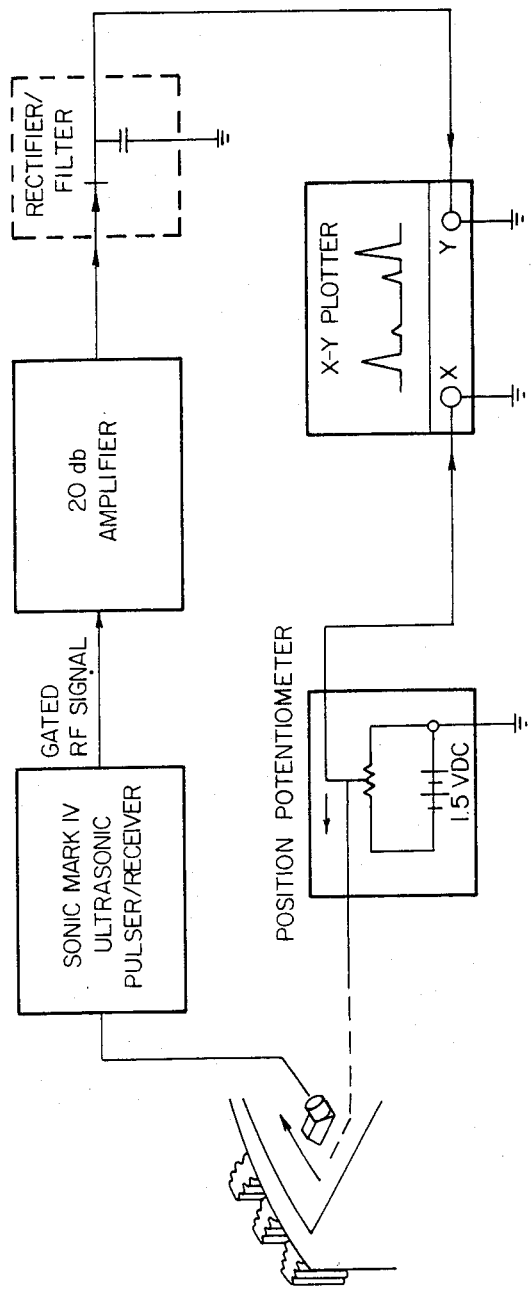
FIG. 11 is a diagram of the apparatus used for detecting Type I and Type II cracks.

As indicated by the scan records of FIGS. 10A and 10B, a continuous record of an inspection scan is preferable in order to indicate the presence of Type II cracks. Accordingly, it becomes advantageous to record the signal amplitude and transducer position as a continuous record. FIG. 11 presents a block diagram of apparatus for making a continuous record of an inspection scan. The apparatus comprises a SONIC Mark IV pulser/receiver providing a gated RF signal to a 20 db amplifier. The amplifier output is routed through a rectifier/filter network before being applied to the Y input of an X-Y plotter. The amplifier is preferably a HP 465A amplifier. The plotter is suitably a Houston Instruments Omnigraphic 2000 X-Y plotter. The transducer position is determined by a Celesco 30-inch position potentiometer. The potentiometer output is applied to the X input of the plotter. The gated RF signal available from the pulser/receiver includes the received crack signal appearing within a small time window or gate. Since crack signal amplitudes are small, the amplifier is used to push the signal to recordable levels. Additionally, to obtain a measure of the signal peak amplitude, the amplified gated RF signal is rectified by the diode and filtered with a 0.005 microfarad capacitor. With regard to the position potentiometer, the slide wire is attached to the transducer fixture and guided along the contour of the steeples so that the resulting signal is linearly proportionally to the examination position on the curved surface of the disc rim.

The foregoing description of the present invention has been directed to particular preferred methods for purposes of explanation and illustration. It will be apparent, however, to those skilled in this art that modifications and changes in methods described may be made without departing from the scope of the invention. For example, other than the preferred skew angles, scan increments, mechanical scanning equipment and electrical equipment may be used. These, and other modifications of the described methods will be apparent to those skilled in this art. It is the applicant's intention of the following claims to cover all such equivalent modifications and variations as fall within the scope of the invention.

What is claimed is:

1. A method of detecting cracks in a turbine disc rim having a web area and adjacent integral, serrated steeples with or without turbine blades mounted therein, comprising the steps of:
   producing an ultrasonic beam of shear waves traveling in a radial direction;
   directing said waves into a steeple from a location on the disc rim web area;
   receiving reflected waves and producing signals indicative thereof;
   displaying the reflected wave signals;
   establishing a predetermined time window on the display based on the time-of-flight difference between the top of the steeple and the disc rim; and
   determining the presence of signals in the display within the time window.

2. The method of claim 1 further comprising the steps of:
   establishing within said time window individual time windows based on the time-of-flight differences between adjacent steeple serrations; and
   determining the presence of signals in the display within the individual time windows.

3. The method of claims 1 or 2 further comprising the step of:
   scanning the disc rim web area with said ultrasonic beam to direct said waves into the steeple along its entire length.

4. A method of detecting cracks in a turbine disc rim having a web area and an adjacent area of integral, serrated steeples with or without turbine blades mounted therein, comprising the steps of:
   producing an ultrasonic beam of shear waves traveling in a radial direction;
   skewing the beam at an acute angle relative to a line normal to the bottom of a steeple;
   directing waves of the skewed ultrasonic beam into the steeple root area from a location on the disc rim web area;
   scanning along the disc rim web with the skewed beam;
   receiving reflected waves as the beam is scanned and producing signals indicative thereof;
   continuously recording the reflected wave signals as the disc rim is scanned to produce a record thereof;
   establishing predetermined time windows on the record based on the time-of-flight to a predetermined, suspected crack location; and
   determining the presence of recorded signals within the time windows.

5. The method of claim 4 wherein the angle of beam skew is 45° in a clockwise rotation from normal.

6. The method of claim 4 wherein the angle of beam skew is 60° in a counter clockwise rotation from normal.

* * * * *